1

United States Patent
Brittain et al.

(10) Patent No.: US 8,685,948 B2
(45) Date of Patent: *Apr. 1, 2014

(54) INTRAVENOUS FORMULATION WITH WATER-SOLUBLE COCRYSTALS OF ACETYLSALICYLIC ACID AND THEANINE

(71) Applicant: Theaprin Pharmaceuticals Inc., Hauppauge, NY (US)

(72) Inventors: Harry G. Brittain, Milford, NJ (US); Philip Felice, Smithtown, NY (US)

(73) Assignee: Theaprin Pharmaceuticals Inc., Hauppauge, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/967,027

(22) Filed: Aug. 14, 2013

(65) Prior Publication Data

US 2013/0345183 A1    Dec. 26, 2013

Related U.S. Application Data

(60) Continuation of application No. 13/617,508, filed on Sep. 14, 2012, which is a division of application No. 13/440,693, filed on Apr. 5, 2012, now Pat. No. 8,304,404, which is a division of application No. 12/437,735, filed on May 8, 2009, now Pat. No. 8,173,625.

(51) Int. Cl.
 *A61K 31/60* (2006.01)
 *A61K 31/12* (2006.01)

(52) U.S. Cl.
 USPC ............................................ 514/165; 514/676

(58) Field of Classification Search
 None
 See application file for complete search history.

*Primary Examiner* — Sreeni Padmanabhan
*Assistant Examiner* — Svetlana M Ivanova
(74) *Attorney, Agent, or Firm* — Notaro, Michalos & Zaccaria P.C.

(57) ABSTRACT

A method of treating rheumatoid arthritis using a water-soluble cocrystal composition contains a quantity of acetylsalicylic acid and a quantity of a theanine enantiomer selected from an alpha variant of theanine or a beta variant of theanine or other form of theanine.

16 Claims, 15 Drawing Sheets

FIG. 1  Photomicrographs taken at two magnifications of the crystalline cocrystal product formed by acetylsalicylic acid and L-theanine.
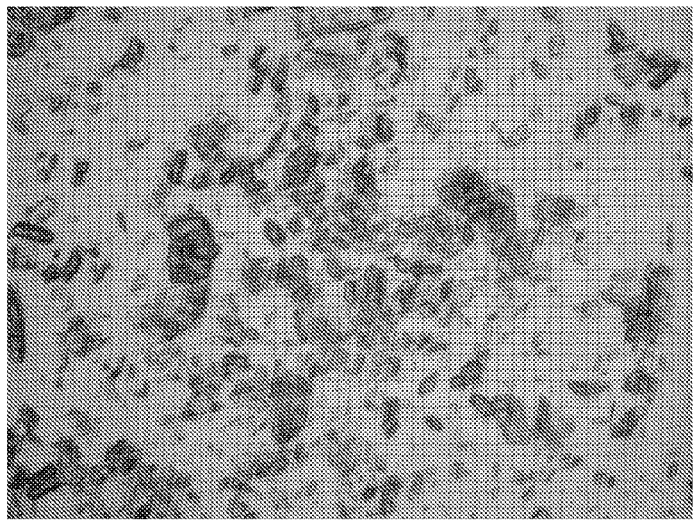
40X
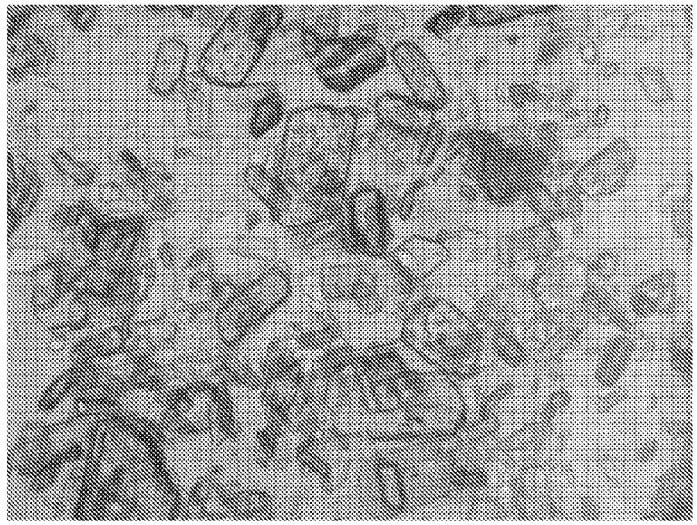
100X FIG. 2   Differential scanning calorimetry thermogram of the cocrystal product formed by acetylsalicylic acid and L-theanine.
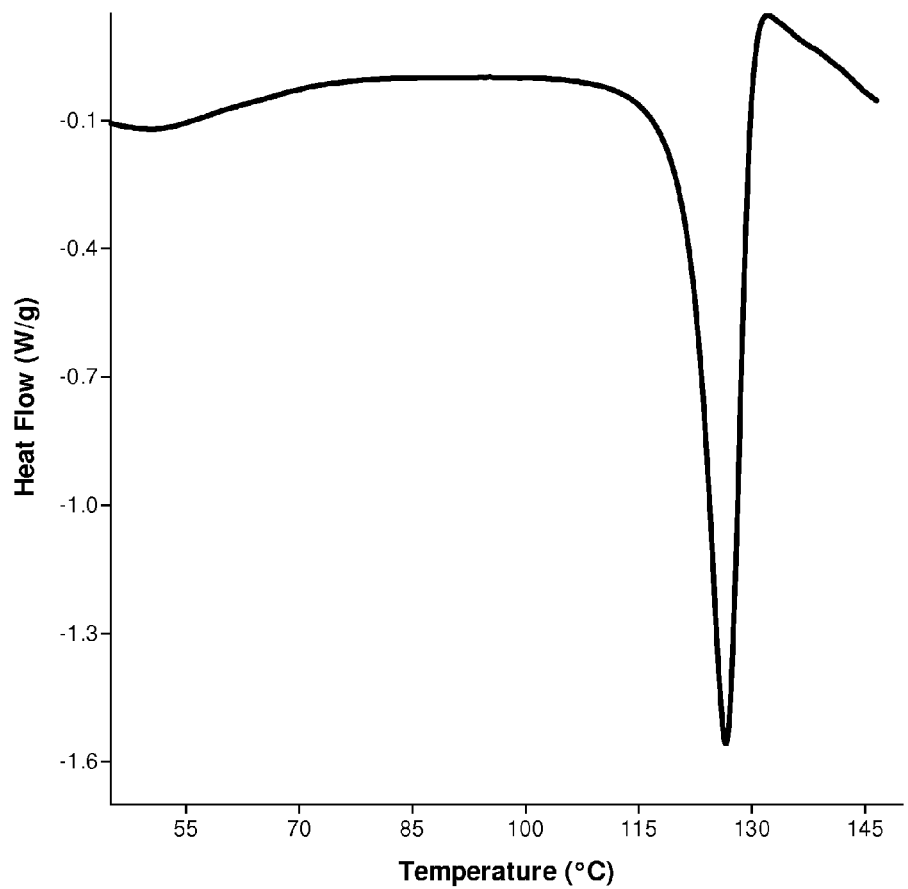

FIG. 3  X-ray powder diffraction pattern of the cocrystal product formed by acetylsalicylic acid and L-theanine.
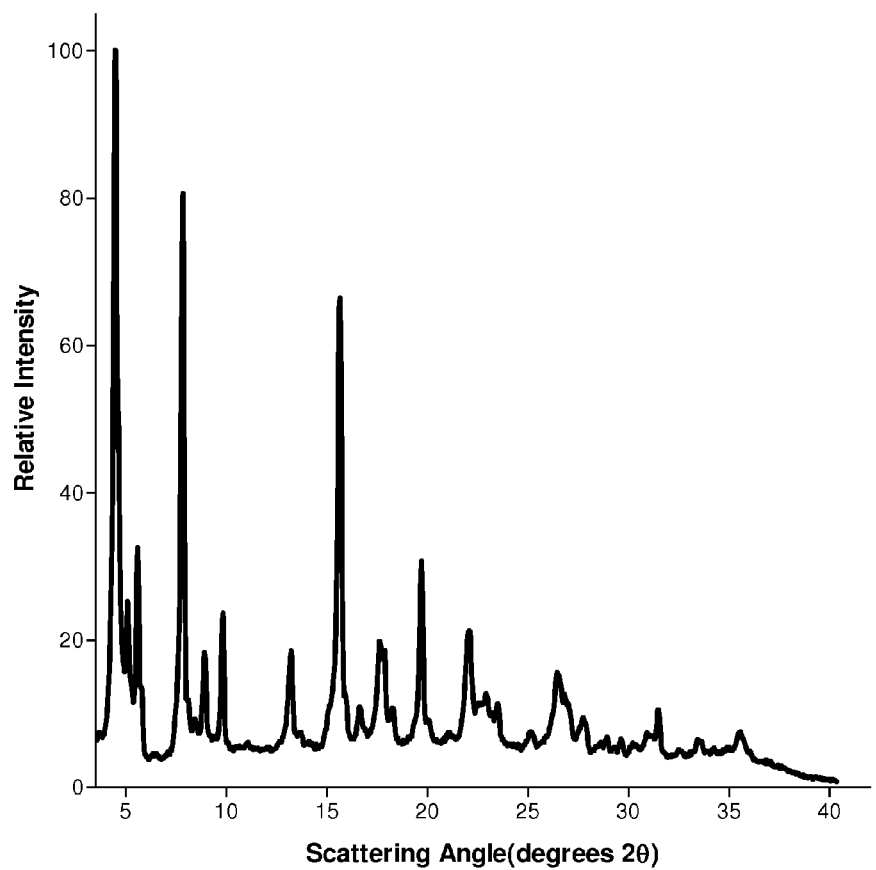

FIG. 4  Infrared absorption spectrum of the cocrystal product formed by acetylsalicylic acid and L-theanine.
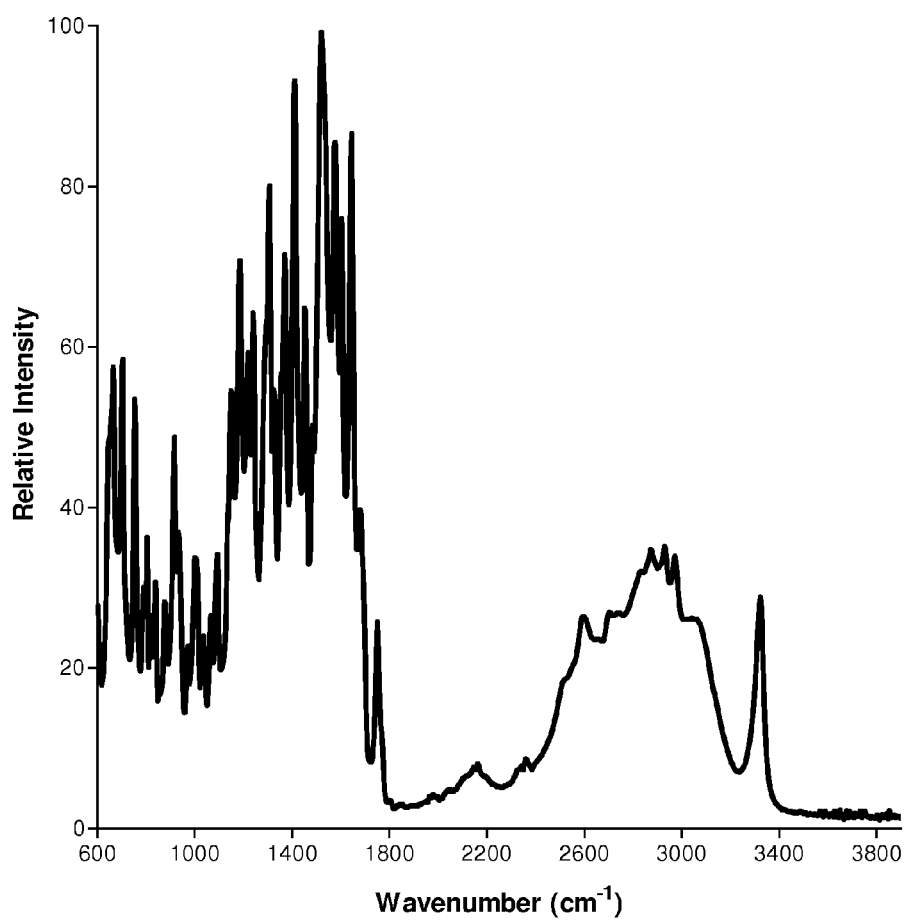

FIG. 5   Raman spectrum of the cocrystal product formed by acetylsalicylic acid and L-theanine.
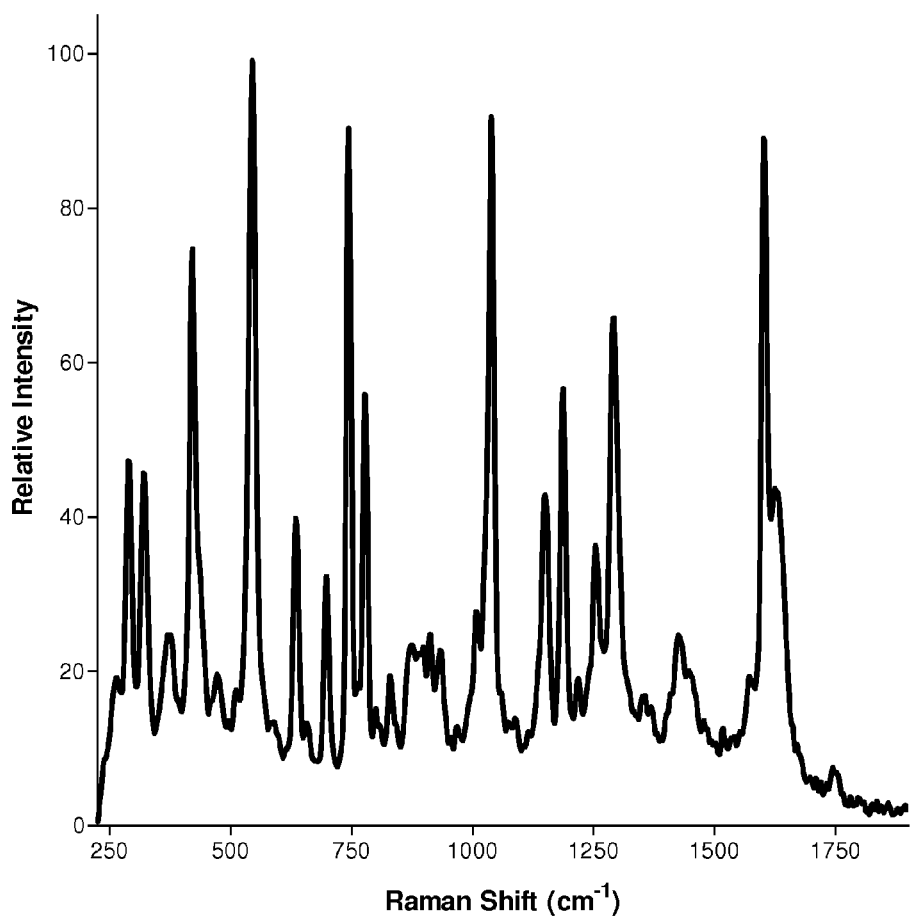

FIG. 6  Photomicrographs taken at two magnifications of the crystalline cocrystal product formed by acetylsalicylic acid and D-theanine.
40X
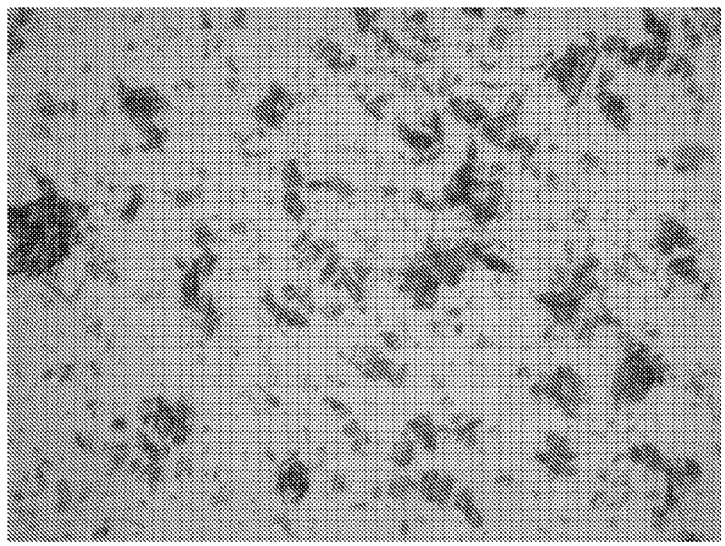
100X
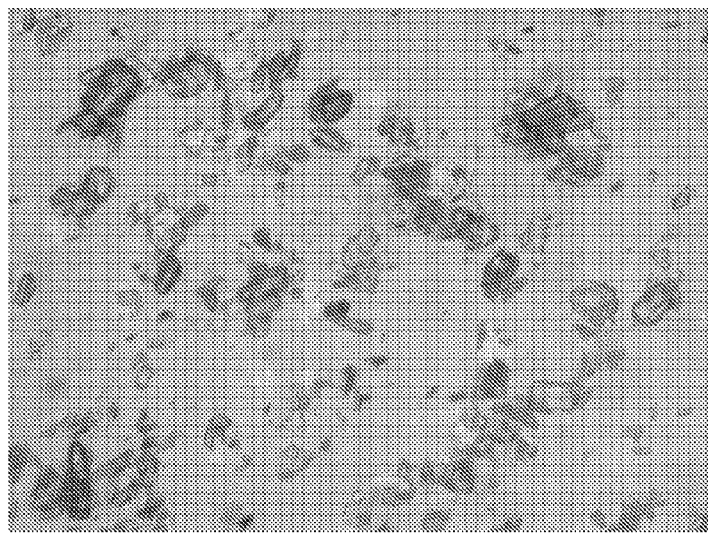

FIG. 7  Differential scanning calorimetry thermogram of the cocrystal product formed by acetylsalicylic acid and D-theanine.
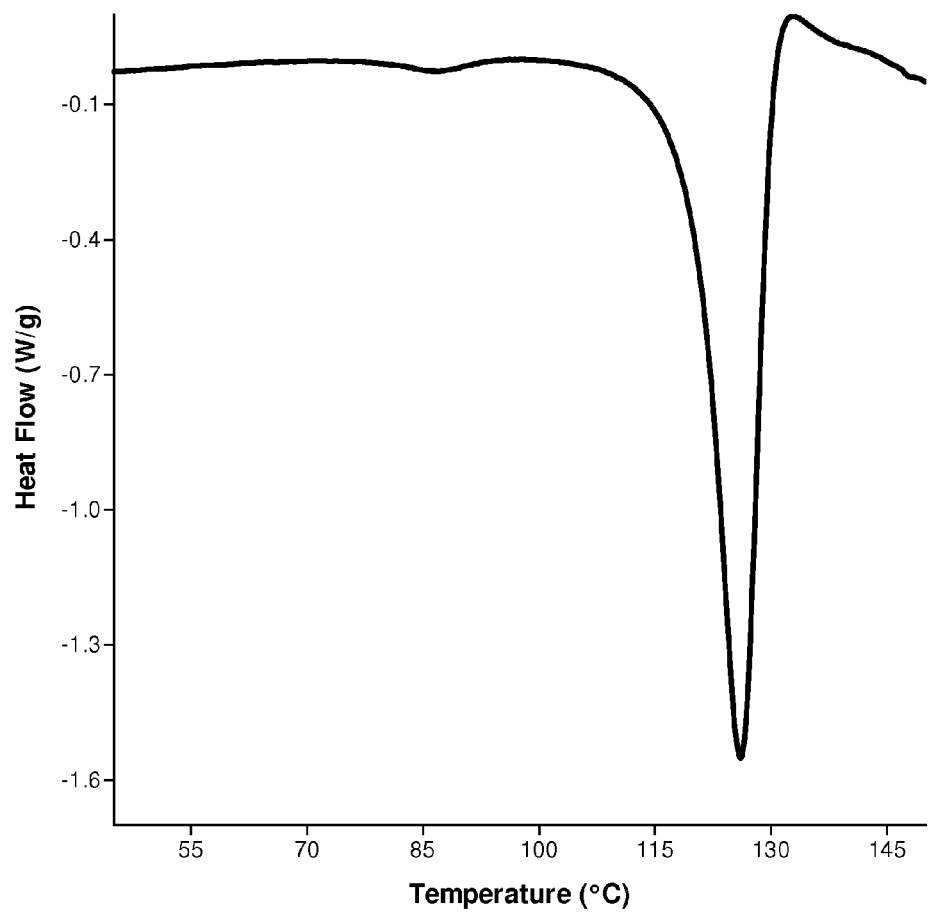

FIG. 8    X-ray powder diffraction pattern of the cocrystal product formed by acetylsalicylic acid and D-theanine.
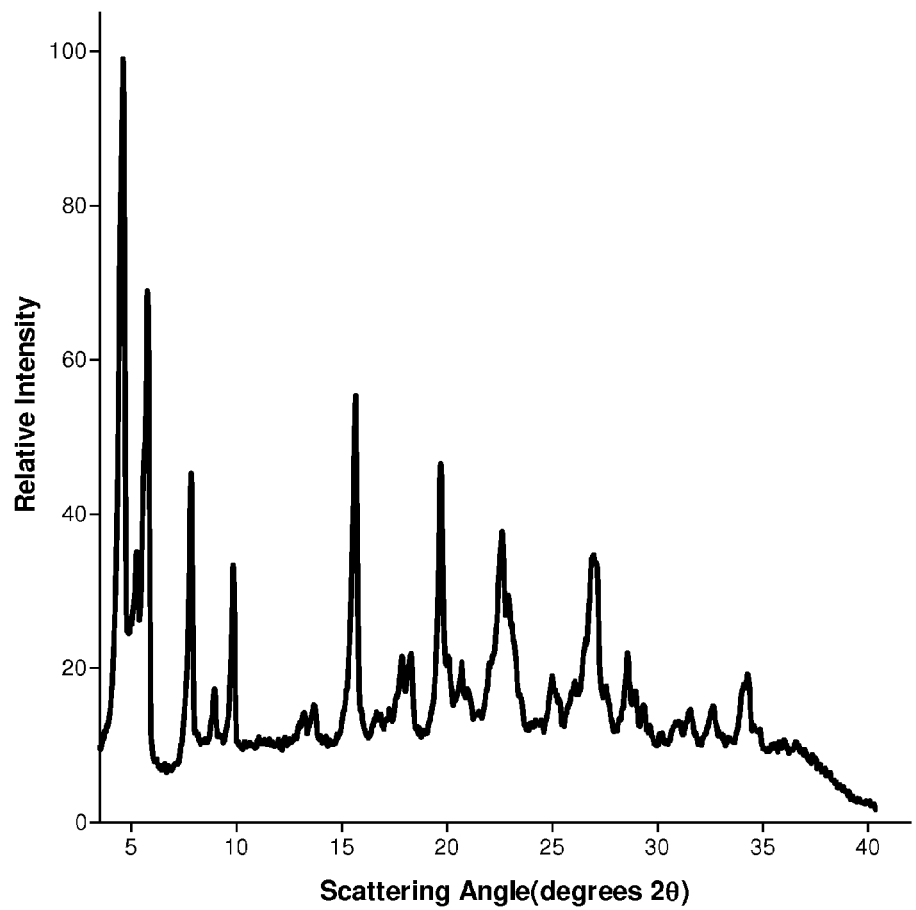

FIG. 9    Infrared absorption spectrum of the cocrystal product formed by acetylsalicylic acid and D-theanine.
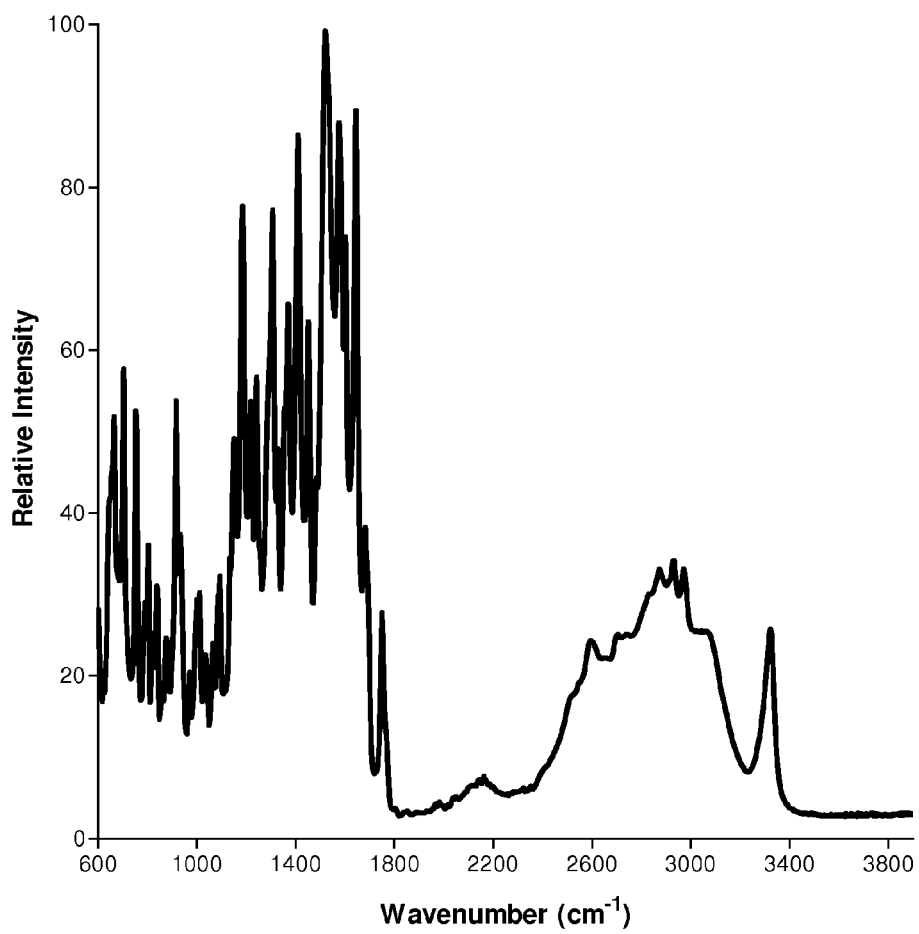

FIG. 10  Raman spectrum of the cocrystal product formed by acetylsalicylic acid and D-theanine.
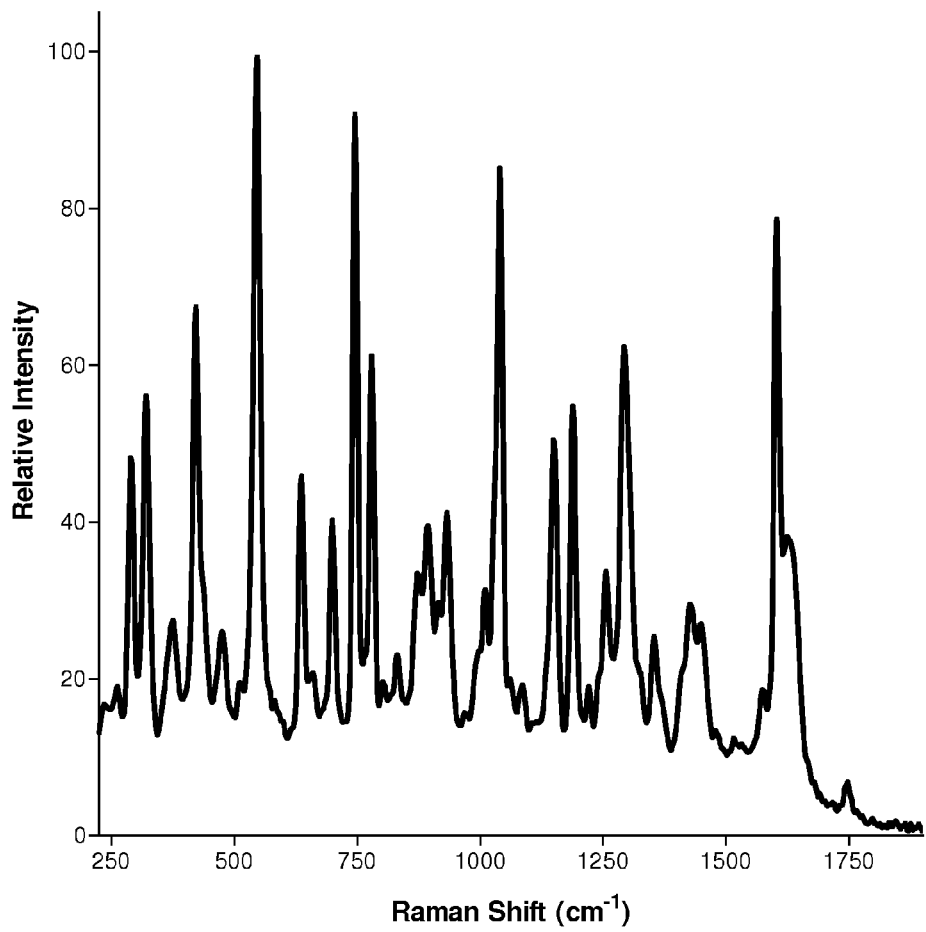

FIG. 11  Photomicrographs taken at two magnifications of the crystalline cocrystal product formed by acetylsalicylic acid and DL-theanine.
40X
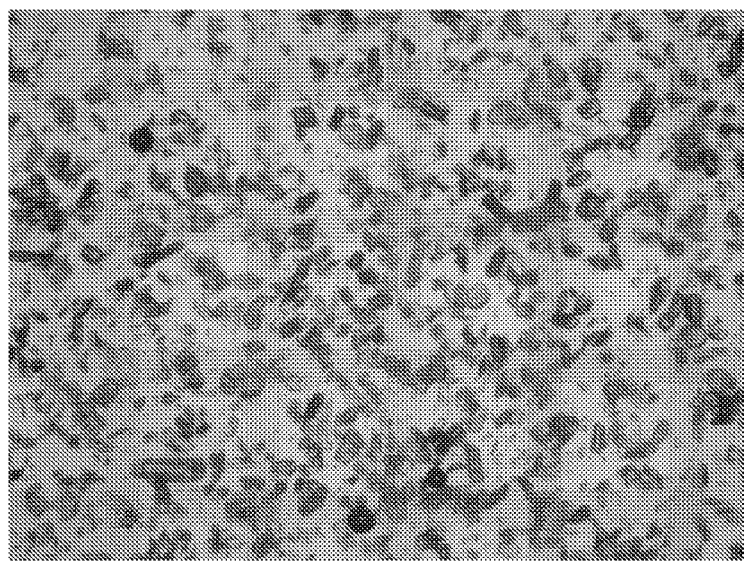
100X
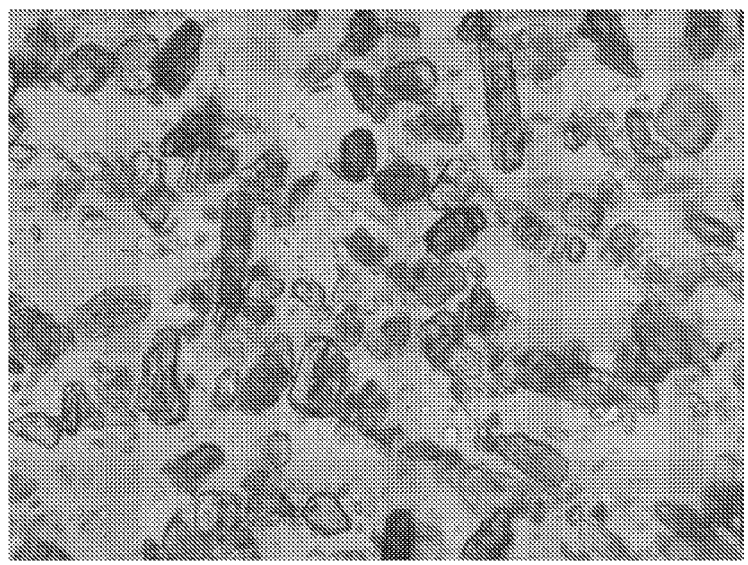

FIG. 12  Differential scanning calorimetry thermogram of the cocrystal product formed by acetylsalicylic acid and DL-theanine.
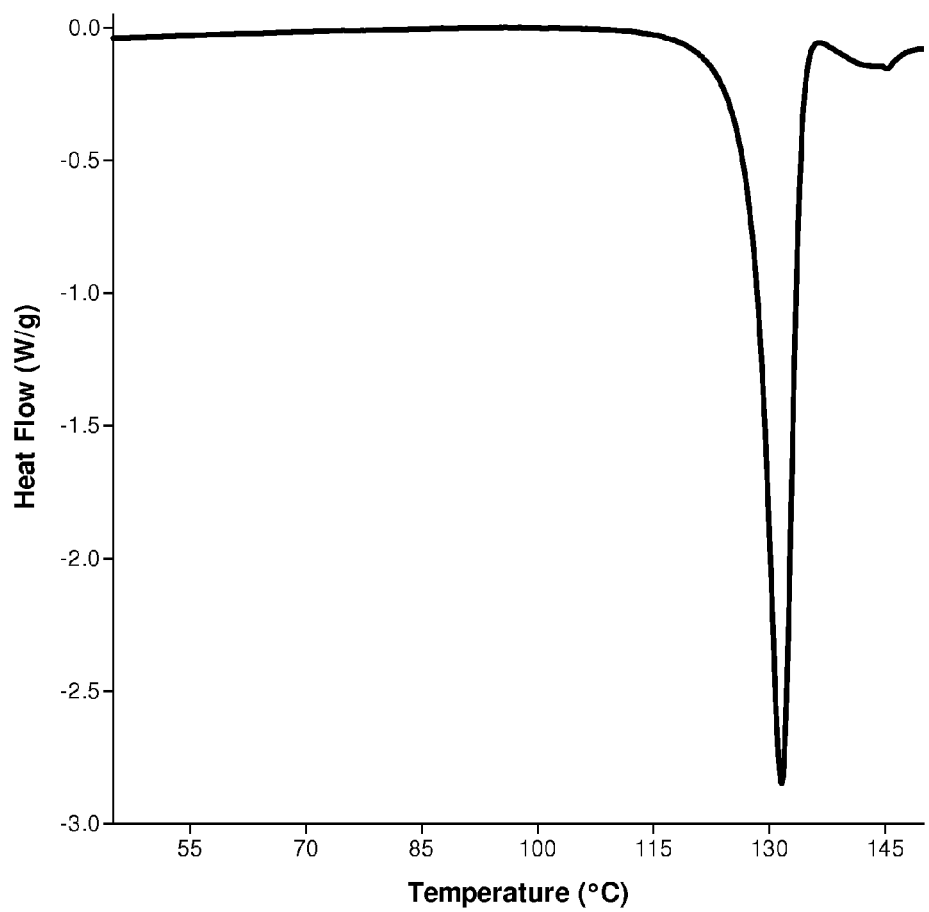

FIG. 13  X-ray powder diffraction pattern of the cocrystal product formed by acetylsalicylic acid and DL-theanine.
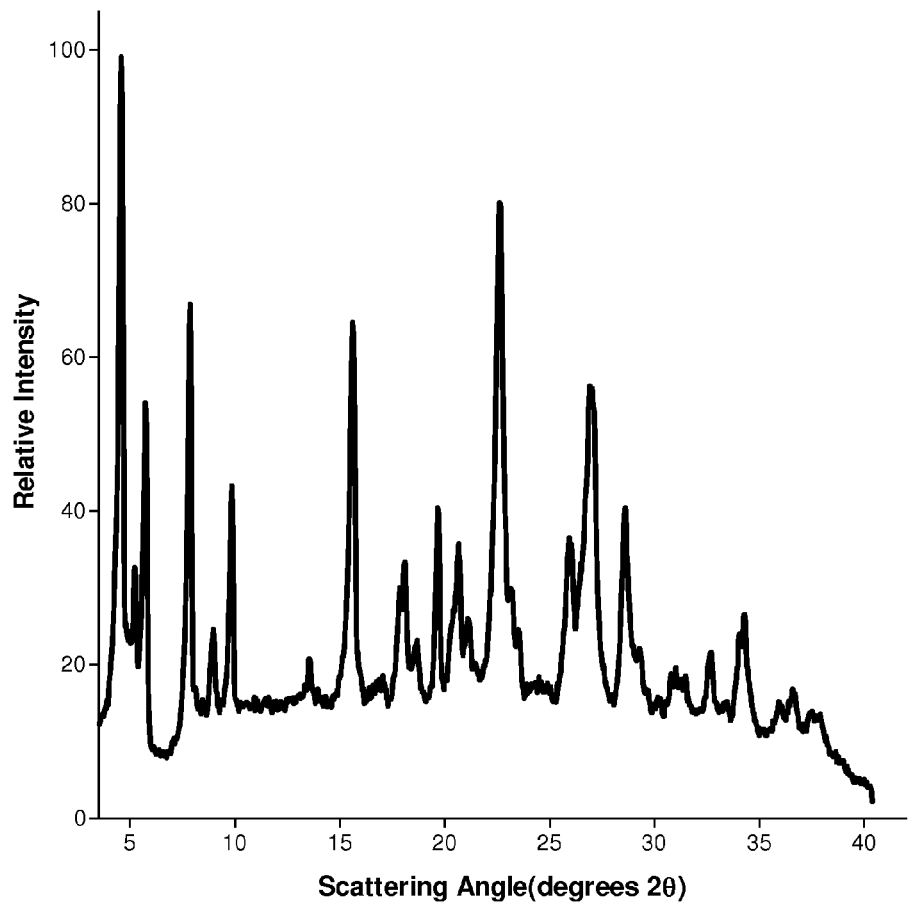

FIG. 14  Infrared absorption spectrum of the cocrystal product formed by acetylsalicylic acid and DL-theanine.
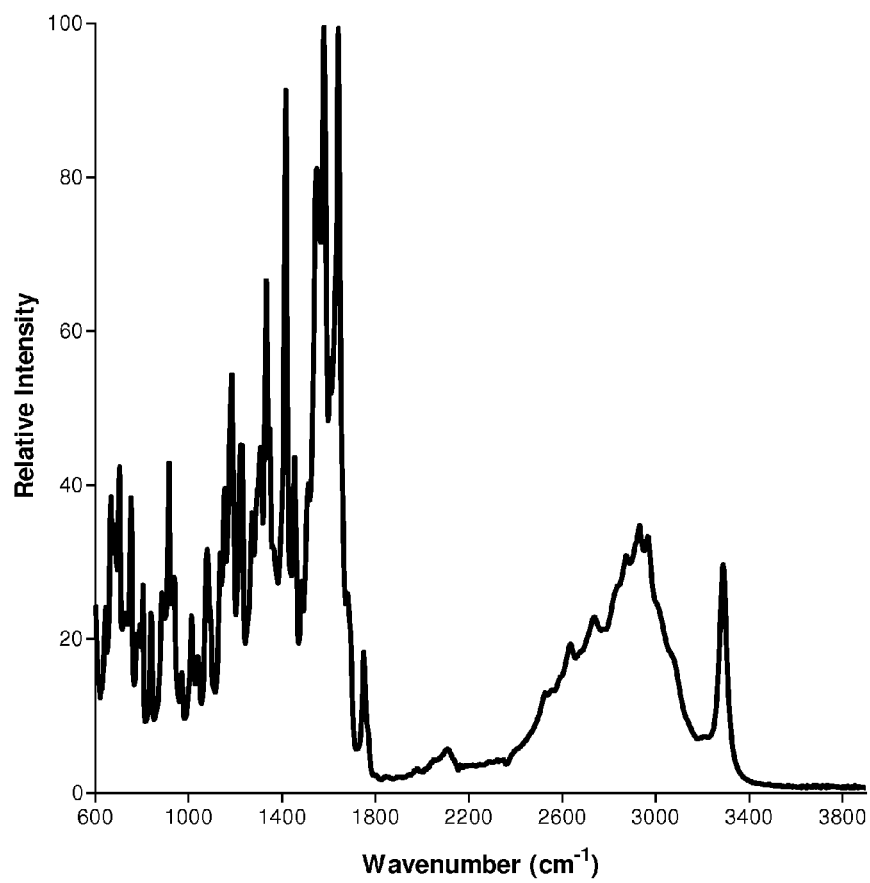

FIG. 15   Raman spectrum of the cocrystal product formed by acetylsalicylic acid and DL-theanine.
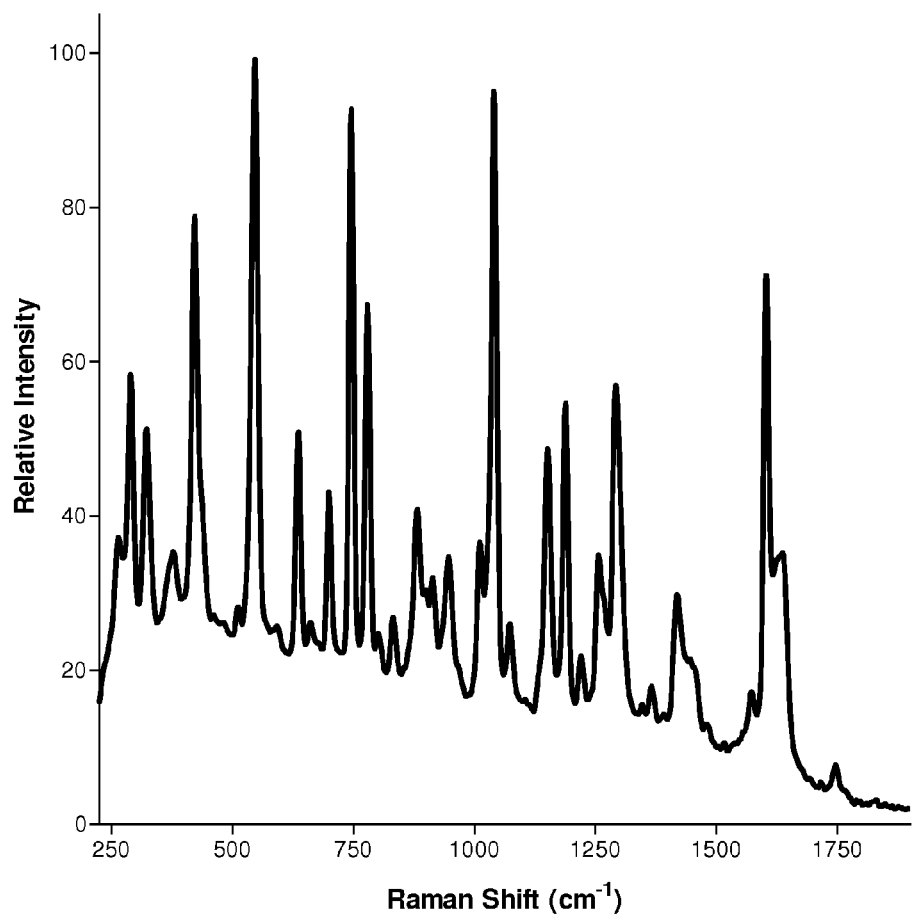

ized in the same way that it is utilized herein. The present invention circumvents these difficulties in a novel and unexpected manner.

INTRAVENOUS FORMULATION WITH WATER-SOLUBLE COCRYSTALS OF ACETYLSALICYLIC ACID AND THEANINE

This application is a continuation of U.S. application no. 13/617,508, filed Sep. 14, 2012, which is a divisional of U.S. application Ser. No. 13/440,693, filed Apr. 5, 2012 and now U.S. Pat. No. 8,304,404 issued Nov. 6, 2012, which is a divisional of U.S. application Ser. No. 12/437,735 filed May 8, 2009 and now U.S. Pat. No. 8,173,625 issued May 8, 2012, which are incorporated herein by reference.

FIELD OF THE INVENTION

The present invention relates to a novel method of administering acetylsalicylic acid, more specifically to a novel intravenous formulation, using a water-soluble cocrystal product of acetylsalicylic acid and theanine that has a neutral pH and provides enhanced stability and bioactivity as compared to previously known water-soluble formulations of aspirin

BACKGROUND OF THE INVENTION

Coronary artery disease is the leading cause of mortality in developed countries. In the United States, a heart attack occurs approximately every 20 seconds. Aspirin inhibition of cyclooxygenase has been shown to be beneficial in patients presenting with acute coronary syndrome and acute myocardial infarction. Researchers found that the median platelet inhibition times for chewed baby aspirin 324 mg, soluble aspirin (alka-seltzer) 325 mg, and whole compressed non-enteric coated aspirin 324 mg, were 7.5 minutes, 7.5 minutes, and 10.0 minutes, respectively. Schwertner, et al, "Effects of different aspirin formulations on platelet aggregation times and on plasma salicylate concentration." *Thromb Res.* 2006; 118(4): 529-34. Epub 2005 Nov. 18. Within 7.5 minutes, though, an individual could be dead from one of a number of potentially fatal arrhythmias such as ventricular tachycardia, ventricular fibrillation or complete heart block. Early administration of a novel intravenous aspirin formulation could start benefitting the patient in a matter of seconds, whereas the full benefit of traditional aspirin may not take effect until major sequelae, complications or death has occurred. In a person presenting with an acute myocardial infarction, intravenous aspirin is the preferred route for early platelet aggregation inhibition. According to the American Heart Association's 2007 National STEMI Statistics, 75% of the nation's acute care hospitals are not capable of performing life-saving PCI (Percutaneous Coronary Intervention) for STEMI (ST elevation myocardial infarction) patients. As such, there is a clear unmet need for a novel intravenous aspirin with improved pharmacokinetics and pharmacodynamics in patients presenting with acute myocardial infarction.

Aspirin inhibits prostanoid biosynthesis, in particular that of thromboxane A2 and prostaglandins PGE2 and PGI2. Aspirin irreversibly inhibits platelet cyclooxygenase 1 (COX-1) through acetylation of the amino acid serine at position 529, thereby preventing arachidonic acid access to the COX-1 catalytic site through steric hindrance. By inhibiting COX-1, the platelet is unable to synthesize prostaglandin H2, which would otherwise be converted to thromboxane A2, which causes platelet aggregation, an early step in the coagulation cascade.

Control of the inflammatory process is regulated by a cascade of biomolecular mechanisms. These mechanisms occur via two pathways: the cyclooxygenase pathway, which results in the formation of prostaglandins, and the lipoxygenase pathway, which results in the formation of leukotrienes. Non-steroid anti-inflammatory drugs (NSAID), like aspirin, function via the cyclooxygenase pathway. There are three major human lipoxygenases. They differ in the position of the double bond on the arachidonic acid molecule. These human lipoxygenases include the 5-, 12-, and 15-lipoxygenases, which respectively catalyze the insertion of oxygen at the C-5, C-12 and C-15 positions of arachidonic acid. The resulting leukotrienes and lipoxins provide signaling molecules associated with a variety of human diseases such as asthma, atherosclerosis, psoriasis and inflammatory bowel disease. Leukotrienes and lipoxins, have been implicated as critical signaling molecules in a variety of cancers. 15-HLO has been shown to be a key biological agent in colorectal cancers, while 12-HLO is involved in pancreatic, breast and prostate cancers. 5-HLO is up-regulated in prostate cancer and its inhibition abolishes all cell proliferation, inducing apoptosis.

Tylenol accounts for most drug overdoses in the United States and other Western countries. The hepatotoxicity of Tylenol (acetaminophen), statins (cholesterol lowering drugs), antiretrovirals (taken for HIV and AIDS), and alcohol are well known. Researchers at Yale University have now provided new insight into the mechanism by which acetaminophen causes liver damage in mice and determined that aspirin provides substantial protection from these toxic effects of acetaminophen. Wajahat Z Mehal; *Acetaminophen-induced hepatotoxicity in mice is dependent on Tlr9 and the Nalp3 Inflammasome; Journal of Clinical Investigation*; Jan. 26, 2009.

Currently, intravenous aspirin is not approved for use in the United States. The poor solubility of aspirin in water and its rapid hydrolysis in the plasma to salicylic acid and acetic acid have limited its intravenous use.

Attempts have been made in the past to produce an aspirin product having an acceptable solubility, but none have proven to be totally satisfactory.

For example, the introduction of Bayer aspirin, as well as Disprin (distributed in the United Kingdom), into water results in the formation of a cloudy suspension indicative of incomplete dissolution in water. Aspro Clear (distributed in Australia and New Zealand and marketed throughout Europe) imparts a non-cloudy, snow globe effect in water for more than three minutes after the tablets have effervesced.

It is well-known that lysine acetylsalicylate (sold as, e.g., Aspegic and Aspisol) is suitable for intravenous administration. The suitability of lysine for intravenous administration is due to the formation of a salt of acetylsalicylic acid with a basic amino acid, with the salt form exhibiting improved solubility. Lysine acetylsalicylate, however, is not approved by the FDA for use in the United States. See e.g., FDA Reports 2006-2008: Aspegic Side-Effect Report #5076936-8 (after drug was administered, patient developed cardio-respiratory arrest and ventricular fibrillation and died); FDA Reports 2006-2008: Aspegic Side Effect Report #5379074-X (after drug was administered, patient experienced angina pectoris and recovered).

U.S. Pat. Nos. 5,665,388 and 5,723,453 to Phykitt, disclose an essentially sodium-free, soluble alkaline aspirin compound. The formulations disclosed in these references, however, suffer from a number of disadvantages. One disadvantage is that the use of bicarbonates, as disclosed therein, causes gas to be formed when ingested by patients. Another disadvantage is that the relatively high pH of the compositions disclosed therein (i.e., greater than 8.0) leads to rapid hydrolysis and instability of the drug substance and, therefore, a shortened shelf-life.

Many of the formulations disclosed in U.S. Pat. Nos. 5,157,030 and 5,776,431 to Galat are formed as two separate compositions (mixture "A" and mixture "B"), which is disadvantageous from manufacturing, packaging and use standpoints. Furthermore, the formulations in these references are blended and then directly added to water. There is no indication that the blended product is stable. Further, compositions formulated in accordance with the Galat patents take up to two to three minutes to substantially completely dissolve in water.

Compositions formulated in accordance with the methods disclosed in Patent Application Publication No. 2006/0292225 to Felix take up to 15-30 seconds to completely dissolve in water with stirring.

Theanine, like aspirin, is known to have salutary effects. It is found in ordinary tea leaves from Camellia sinensis and the mushroom Xerocomus badius, but is otherwise rare in nature. Preliminary research, suggests that L-theanine promotes alpha wave generation in the brain. Thereby, an awake, alert and relaxed physical and mental condition is achieved, which demonstrates theanine's effectiveness in stress management. L-theanine does not cause drowsiness or impair a person's motor skills. It has been shown to work antagonistically against the negative side effects of caffeine, to increase dopamine and serotonin concentrations in the brain, to be effective in reducing the hypertension and disturbance of sleep often associated with the use of caffeine, and to diminish symptoms of premenstrual syndrome. Laboratory studies indicate that theanine produces these effects by increasing the level of GABA (gamma-aminobutyric acid), an important inhibitory neurotransmitter in the brain.

It has been reported that theanine supports the immune system and may reduce plasma total cholesterol, cholesterol ester and very-low-density lipoprotein cholesterol.

Studies on the effects of theanine on alcohol metabolism and hepatic toxicity have shown that theanine is effective against alcoholic liver injury.

Theanine also has the potential to protect neurons from excesses of glutamate. Glutamate is an essential brain chemical that may be released in excess amounts with some disease conditions (e.g., amyotrophic lateral sclerosis and cerebrovascular dementia) and with brain injuries, as occurs with strokes or physical injuries. Theanine may protect against this damage by blocking glutamine entrance to cells due to the similarity in the stereochemical structures of theanine and glutamine.

A direct metabolite of amino acids glutamine and glutamic acid, theanine is made different by its ethyl-N alkylation of glutamine's nitrogen. The amino acid scaffolds glutamine and its metabolite glutamic acid provide the general, alpha amino acid core structure responsible for theanine's transport, while ethyl-N alkylation of glutamine provides both its transport and pharmacological properties. The similarity of glutamine's and glutamic acid's structure with theanine allows theanine to be substrate and product competitors for all physiological glutamine and glutamic acid reactions, providing their charges are similar. Therefore, wherever glutamine or glutamic acid is a metabolite, theanine can activate, inhibit or add to target activity. This is why its effects are so far-reaching. It is a glutamine mimetic with pharmacological activity. Glutamine is a significant consumer of ATP for nitrogen incorporation, which may explain some of the anti-cancer and anti-HIV activity of theanine. If N-fixation is inhibited, cell or viral structure growth is also inhibited.

The amino acids glutamine and glutamic acid have common molecular elements with theanine. Some examples of common molecular elements are pI(isoelectric point), polarity, hydropathy index, and elements that support their role as metabolite targets for theanine. The overlapping molecular properties allow theanine to function as a glutamine or glutamic acid analogue. These properties relate to the electrostatic profile of theanine under physiological conditions and its overall structural geometry, which includes atoms common to the related core amino acids glutamine and glutamic acid. The coincident array of atoms and the relative electrostatic structure of glutamine and glutamic acid allow them to serve as targets for theanine. The targets also include the enzymes, proteins, receptors or other macromolecules they effectively bind. In the case of glutamic acid, the atoms that make up the isosteric structure up to the C5 or gamma carboxyl are in the same array as theanine. In the case of glutamine, the isosteric and isoelectronic atoms of glutamine are equal to theanine's where hydrogen has been replaced by ethyl ($-C_2H_5$) on the carboxamide nitrogen of glutamine.

Glutathione is the liver's first-line defense against drugs and chemicals. It is used by cancer cells against drugs and chemicals. Cancer cells use glutathione to detoxify doxorubicin and escort the drug out of cells. Theanine is able to interfere with this process due to its structural similarity to glutamate. Glutamic acid, or glutamate, is one of the components of glutathione, the drug detoxifier. Because it looks like glutamic acid, cancer cells take up and mistakenly use the theanine to create glutathione. But the glutathione they create with theanine does not detoxify like natural glutathione. Instead, this theanine-based glutathione appears to block the ability of cancer cells to detoxify.

Further, in addition to enhancing doxorubicin's cancer-killing effects without harming healthy tissue, theanine also keeps doxorubicin out of healthy tissue. This is a major added benefit, since one of the drawbacks of the use of doxorubicin is its toxicity to the heart. The potential of theanine as an adjunct to cancer chemotherapy was proposed by researcher Yasuyuki Sadzuka, who confirmed that theanine, a major amino acid in green tea, enhances the antitumor activity of doxorubicin (DOX) without an increase in DOX-induced side effects. He postulated that the action of theanine is due to decreases in glutamate uptake via inhibition of the glutamate transporter and reduction of glutathione and DOX export from the cell. Theanine enhances the antitumor activity not only of DOX but also of cisplatin and irinotecan (CPT-11). In essence, Sadzuka found that theanine could block the export of doxorubicin (Adriamycin) from cancer cells by blocking the glutamate and glutathione transporter mechanisms; the elevated level of the drug within cancer cells strongly inhibits the tumor. Sadzuka Y, et al., "The effects of theanine, as a novel biochemical modulator, on the antitumor activity of adriamycin," *Cancer Letters* 1996; 105(2): 203-209; Sadzuka Y, et al., "Modulation of cancer chemotherapy by green tea," *Clinical Cancer Research* 1998; 4(1): 153-156; Sadzuka Y, et al., "Efficacies of tea components on doxorubicin induced antitumor activity and reversal of multidrug resistance," *Toxicology Letters* 2000; 114 (1-3): 155-162; Sadzuka Y, et al., "Improvement of idarubicin induced antitumor activity and bone marrow suppression by theanine, a component of tea," *Cancer Letters* 2000; 158(2): 119-24; Sadzuka Y, et al., "Enhancement of the activity of doxorubicin by inhibition of glutamate transporter," *Toxicology Letters* 2001; 123(2-3): 159-67; Sadzuka Y, et al., "Effect of dihydrokainate on the antitumor activity of doxorubicin," *Cancer Letters* 2002; 179 (2): 157-163.

Therapeutic compounds, such as aspirin, are most stable in a crystalline form, but can display poor aqueous solubilities and slow dissolution rates. These properties impart the tendency to reduce the bioavailability of the active pharmaceutical ingredient (API), thereby slowing absorption.

A cocrystal is a multiple-component crystal, in which two or more molecules associate (but do not bond) on the molecular level in solid crystalline form under ambient conditions. They are attractive to the pharmaceutical industry because they offer opportunities to modify the chemical and/or physical properties of an API without the need to make or break covalent bonds. In pharmaceutical cocrystals, the molecular structure of the API is not changed. This has important implications for streamlined regulatory approval of new forms. By their very nature, APIs, molecules that contain exterior hydrogen-bonding moieties, are predisposed to formation of cocrystals. Pharmaceutical cocrystals will afford forms of APIs with improved physical properties such as solubility, stability, hygroscopicity, and dissolution rate. Physical properties are not just dependent upon molecular structure. They are also critically dependent upon supramolecular chemistry and its influence upon crystal structure. The application of the concepts of supramolecular synthesis and crystal engineering to the development of pharmaceutical cocrystals offers many opportunities related to drug development and delivery.

Thus, a water-soluble aspirin-theanine cocrystal composition which has enhanced stability and bioactivity as compared to previously-known, water-soluble analgesic compositions, and which delivers the salutary effects of both aspirin and theanine, is needed.

The present invention satisfies these and other medical needs and overcomes deficiencies found in the prior art.

SUMMARY OF THE INVENTION

Accordingly, it is an object of the present invention to provide a water-soluble aspirin-theanine cocrystal composition having a crystalline structure and which has enhanced stability and bioactivity, as compared to previously-known, water-soluble analgesic compositions.

A further object of the present invention is to provide a water-soluble aspirin-theanine cocrystal composition having the above characteristics and which is rapidly water-soluble.

Yet a further object of the present invention is to provide a water-soluble aspirin-theanine cocrystal composition having the above characteristics and which may be used in the relatively large dosages that are required for anti-inflammatory treatment.

It is an object of the present invention to provide a method of administering a water-soluble aspirin-theanine cocrystal composition intravenously in humans that has a neutral pH, provides enhanced stability and bioactivity, and is suitable for treatment of various diseases and medical conditions.

Still another object of the present invention is to provide aqueous aspirin-theanine cocrystal formulations suitable for intravenous administration having the above characteristics and which allow for rapid delivery of acetylsalicylic acid to the bloodstream.

Yet a further object of the present invention is to provide aqueous aspirin-theanine cocrystal formulations suitable for intravenous administration having the above characteristics and which may be used for extended periods of time without causing the gastrointestinal upset and/or erosions, bleeding, or perforation of the gastrointestinal tract which may occur with conventional oral aspirin.

Another object of the present invention is to provide aqueous aspirin-theanine cocrystal formulations suitable for intravenous administration having the above characteristics and which allow for delivery of therapeutic quantities of theanine to the bloodstream.

These and other objects of the present invention are achieved in accordance with one embodiment of the present invention by provision of a water-soluble aspirin-theanine cocrystal composition which includes a quantity of acetylsalicylic acid and a quantity of a theanine enantiomer associated with the quantity of acetylsalicylic acid, the cocrystal composition being formed by physically combining the quantity of acetylsalicylic acid and the quantity of a theanine enantiomer into a mixture and wetting the mixture with a quantity of a wetting agent and grinding the combination for a length of time sufficient to produce a dried-crystalline mass. In some embodiments, the wetting agent employed is methanol.

Formulations according to embodiments of the present invention protect aspirin from hydrolysis, with the bulk active ingredient being a well-defined, free-flowing crystalline solid which has enhanced stability and bioactivity. The solid has a solubility in water of about 10 mg/mL, and yields a clear aspirin solution shortly after being mixed.

Compositions according to embodiments of the present invention are very soluble in water, requiring about less than one part water per part solute, especially when compared to traditional aspirin, which is only very slightly soluble, requiring about 1,000 to 10,000 parts water per part solute.

In accordance with an embodiment of the present invention, a method of creating a water-soluble aspirin-theanine cocrystal composition includes the steps of (i) providing a quantity of acetylsalicylic acid; adding a quantity of a theanine enantiomer to the quantity of acetylsalicylic acid to form a mixture comprising the quantity of acetylsalicylic acid and the enantiomer of theanine; (ii) wetting the mixture; and (iii) grinding the mixture for a length of time sufficient to produce a dried crystalline mass. In certain of these embodiments, methanol is employed in the step of wetting the mixture. In certain of these embodiments, the dried crystalline mass has an aqueous solubility of at least about 9.0 mg/mL.

In some embodiments of the present invention the quantity of acetylsalicylic acid falls within the range of about 5% to 95% by weight of the mixture of the quantity of acetylsalicylic acid and the quantity of a theanine enantiomer. In other embodiments, the quantity of acetylsalicylic acid falls within the range of about 15% to 85% by weight of the mixture of the quantity of acetylsalicylic acid and the quantity of a theanine enantiomer. In further embodiments, the quantity of acetylsalicylic acid is about 50% by weight of the mixture of the quantity of acetylsalicylic acid and the quantity of a theanine enantiomer.

In some of these embodiments, the theanine enantiomer is the L-form. In other embodiments, the theanine enantiomer is the D-form. In further embodiments, the theanine enantiomer is the DL-form.

In some of these embodiments, the resultant aspirin-theanine cocrystal composition is dissolved in a solvent to form an aspirin-theanine cocrystal solution. In certain of these embodiments, the solvent is water. In certain of these embodiments, the resultant aspirin-theanine cocrystal solution has a pH that is physiologic. In certain of these embodiments, the resultant aspirin-theanine cocrystal solution has a pH in the range of about 7.35 to about 7.45. In certain of these embodiments, the resultant aspirin-theanine cocrystal solution has a pH which is about 7.4.

In accordance with another embodiment of the present invention, a method of creating a water-soluble aspirin-theanine cocrystal composition includes the steps of: (i) providing a quantity of acetylsalicylic acid; (ii) adding a quantity of an enantiomer of theanine to said quantity of acetylsalicylic acid to form a mixture comprising said quantity of acetylsalicylic acid and said enantiomer of theanine; (iii) dissolving said combination in a quantity of a solvent to form a solution; and (iv) drying said solution for a length of time sufficient to produce a dried crystalline mass. In certain of these embodiments, the dried crystalline mass has an aqueous solubility of at least about 9.4 mg/mL. In certain of these embodiments, water is employed as the solvent. In certain of these embodiments, the drying step is performed by means of a rotary evaporation process.

In certain of these embodiments, the theanine enantiomer is the L-form. In some of these embodiments the theanine enantiomer is the D-form. In further of these embodiments, the theanine enantiomer is the DL-form.

In some embodiments of the present invention, the theanine enantiomer further comprises a carbohydrate functional group thereon. In these embodiments, the carbohydrate functional group may be of the L-configuration or the D-configuration. In these embodiments, the carbohydrates employed may be monosaccharides, disaccharides, trisaccharides, oligosaccharides or polysaccharides.

In some embodiments of the present invention, the theanine enantiomer further comprises an amino acid functional group thereon. In certain of these embodiments, the amino acid functional group is a dipeptide.

The various features of novelty which characterize the invention are pointed out with particularity in the claims annexed to and forming a part of this disclosure. For a better understanding of the invention, its operating advantages and specific objects attained by its uses, reference is made to the accompanying figures and descriptive matter in which a preferred embodiment of the invention is illustrated.

BRIEF DESCRIPTION OF THE DRAWINGS

In the drawings:

FIG. 1 depicts photomicrographs taken at two magnifications of the crystalline cocrystal product formed by acetylsalicylic acid and L-theanine according to embodiments of the present invention;

FIG. 2 is a differential scanning calorimetry thermogram of the cocrystal formed by acetylsalicylic acid and L-theanine according to embodiments of the present invention;

FIG. 3 is an x-ray powder diffraction pattern of the cocrystal formed by acetylsalicylic acid and L-theanine according to embodiments of the present invention;

FIG. 4 is an infrared absorption spectrum of the cocrystal formed by acetylsalicylic acid and L-theanine according to embodiments of the present invention;

FIG. 5 is a Raman spectrum of the cocrystal formed by acetylsalicylic acid and L-theanine according to embodiments of the present invention;

FIG. 6 depicts photomicrographs taken at two magnifications of the crystalline cocrystal product formed by acetylsalicylic acid and D-theanine;

FIG. 7 is a differential scanning calorimetry thermogram of the cocrystal formed by acetylsalicylic acid and D-theanine according to embodiments of the present invention;

FIG. 8 is an x-ray powder diffraction pattern of the cocrystal formed by acetylsalicylic acid and D-theanine according to embodiments of the present invention;

FIG. 9 is an infrared absorption spectrum of the cocrystal formed by acetylsalicylic acid and D-theanine according to embodiments of the present invention;

FIG. 10 is a Raman spectrum of the cocrystal formed by acetylsalicylic acid and D-theanine according to embodiments of the present invention;

FIG. 11 depicts photomicrographs taken at two magnifications of the crystalline cocrystal product formed by acetylsalicylic acid and DL-theanine;

FIG. 12 is a differential scanning calorimetry thermogram of the cocrystal formed by acetylsalicylic acid and DL-theanine according to embodiments of the present invention;

FIG. 13 is an x-ray powder diffraction pattern of the cocrystal formed by acetylsalicylic acid and DL-theanine according to embodiments of the present invention;

FIG. 14 is an infrared absorption spectrum of the cocrystal formed by acetylsalicylic acid and DL-theanine according to embodiments of the present invention; and FIG. 15 is a Raman spectrum of the cocrystal formed by acetylsalicylic acid and DL-theanine according to embodiments of the present invention.

DESCRIPTION OF THE PREFERRED EMBODIMENTS

The present invention satisfies needs left unresolved by the prior art by providing a method for synthesizing a soluble cocrystal formed by acetylsalicylic acid and L-theanine which is readily administerable to individuals through a variety of media.

Embodiments of the present invention employ L-theanine, a rare amino acid. L-theanine is a water-soluble, white crystalline powder, having a Chemical Abstracts Service (CAS) Registry Number of 3081-61-6 and a GRAS classification (GRAS Notice Number: GRN 000209). L-theanine has the empirical formula $C_7H_{14}N_2O_3$, a molecular weight of 174.20, and the systematic name of 2-Amino-4-(ethylcarbamoyl)butyric acid. Being 5-N-ethyl glutamine, theanine differs from glutamine by the CH2—CH3 (ethyl) group (replacing hydrogen). N-Ethyl confers on theanine its active properties.

Embodiments of the present invention include cocrystals of acetylsalicylic acid with theanine (5-N-ethyl-glutamine). Further, the theanine contained in compositions according to embodiments of the present invention may be of any of L-form, D-form, DL-form.

Embodiments of the present invention may include the amino acid scaffolds glutamine and/or glutamic acid.

Non-limiting examples of enantiomers utilized in embodiments according to the present invention may include a D-enantiomer of Theanine, D-Glu(NHEt)-OH, 2R enantiomer; an L-enantiomer of Theanine, L-Glu(NHEt)-OH, 2R enantiomer; a DL enantiomer of Theanine, DL-Glu(NHEt)-OH enantiomer; a D-enantiomer of Theanine, D-Gln(Et)-OH, 2R enantiomer; an L-enantiomer of theanine, L-Gln(Et)-OH, 2R enantiomer; and a DL-enantiomer of theanine, DL-Gln(Et)-OH, 2R enantiomer. The purity percentages of the D-enantiomers of theanine, D-Glu(NHEt)-OH, 2R enantiomer and D-Gln(Et)-OH, 2R enantiomer; the L enantiomers of theanine, L-Glu(NHEt)-OH, 2R enantiomer and L-Gln (Et)-OH, 2R enantiomer; and the DL-enantiomers of theanine, DL-Glu(NHEt)-OH, 2R enantiomer and DL-Gln(Et)-OH, 2R enantiomer in compositions according to embodiments of the present invention is 99+%; 99+% 2R enantiomer. The D-enantiomer at 99+%; 99+% ee % (2R) is where the first measure is the overall chemical purity (hplc) and where the second measure is ee % (2R) known as the "percent enantiomeric excess." The % ee is the measure of chiral purity equal to [% R-%S%/=/]*100 defined by the ratios of their diasteriomeric derivatives. Purity percentages may range from 90% to 99.99% in any D or L configuration of any theanine or any enantiomer thereof.

Embodiments of the present invention may include cocrystal compositions of acetylsalicylic acid and alpha variants of L-theanine, acetylsalicylic acid and alpha variants of D-theanine, and acetylsalicylic acid and alpha variants of DL-theanine.

Non-limiting examples of alpha variants used in embodiments according to the present invention may include L-northeanine, D-northeanine, DL-northeanine, L-homotheanine, D-homotheanine, DL-homotheanine L-bishomotheanine, D-bishomotheanine, and DL-bishomotheanine, i.e., the respective C-1, C+1, and C+2 homologous analogues of theanine.

According to embodiments of the present invention the L-, D-, DL-alpha amino acids of theanine and their side-chain carbon homologues (nor, homo, and bishomologues) may have a functional R— group, where R1 may contain linear, cyclic, or branched alkyl groups and derivatives thereof; linear, cyclic, or branched alkenyl groups and derivatives thereof; and aromatic radicals and derivatives thereof. In embodiments of the present invention, the aromatic radicals may be aryl radicals.

According to the embodiments of the present invention the single enantiomers (S and R) and racemic forms (S, R-mixture) of the beta amino acids of theanine may have a functional R-group, where R1 may contain linear, cyclic, or branched alkyl groups and derivatives thereof; linear, cyclic, or branched alkenyl groups and derivatives thereof; and aromatic radicals and derivatives thereof. In embodiments of the present invention, the aromatic radicals may be aryl radicals.

Embodiments of the present invention may include cocrystal compositions of acetylsalicylic acid and the enantiomers, L- and D-isomers, D, L-racemic mixture, S- and R-isomers, S, R-racemic mixtures, all rotamers, tautomers, salt forms, and hydrates of the alpha and beta amino acids of theanine in which the N-substituted functional R1— group [C4 or gamma-CH2—C(O)—NR1] may contain linear, cyclic, or branched alkyl groups and derivatives thereof; linear, cyclic, or branched alkenyl groups and derivatives thereof; and aromatic radicals and derivatives thereof making up all the analogue forms of theanine. In embodiments of the present invention, the aromatic radicals may be aryl radicals.

An aqueous solution is a solution in which water is the dissolving medium or solvent, and which is essentially free of colloidal solids. Dissolved crystals form true solutions and are capable of passing through a semi-permeable membrane as in dialysis, whereas colloids are unable to pass through a semi-permeable membrane. The compositions according to embodiments of the present invention form a true solution when dissolved in water, are able to pass through a semi-permeable membrane, and can be used in dialysis. Examples of aqueous solutions that may be used in embodiments of the present invention include pure water, and the following: D5W, D10W, D50, D5 0.3% NS, D5 0.45% NS, 0.45% NS, D5 0.9% NS, 0.9% NS, 3% NaCl, D5RL, LR, NaHCO$_3$, and Xylitol solutions.

Solutions formed by dissolving acetylsalicylic acid-theanine cocrystal compositions according to embodiments of the present invention in water do not contain colloidal particles, and hence, do not exhibit the strong Tyndall effect characteristic of colloidal dispersions.

It should be understood that the term "suitable," as it is used herein, generally refers to the fact that the solution can be administered intravenously to humans, without causing unfavorable side effects.

The effective amount of acetylsalicylic acid administered to a patient (i.e., the amount that will have a salutary effect with regards to a disease or condition being treated) will be influenced by gender, age, weight, body fluid status, severity of the disease or condition being treated, liver enzyme function, and renal excretion of salicylate which, in turn, is dependent upon urine pH, and protein binding of salicylates, which is concentration-dependent.

The term "carbohydrate," as it is used herein, generally refers to simple organic compounds that are aldehydes or ketones substituted with multiple hydroxyl groups, of the general formula $(CH_2O)_n$, where n is any number of three or greater.

Monosaccharides, disaccharides, trisaccharides, oligosaccharides, polysaccharides, dipeptides, and combinations of these may be used with the acetylsalicylic acid—theanine cocrystal compositions according to embodiments of the present invention, in particular, with those cocrystals formed according to the steps applied in Examples 1-8 below.

Compositions according to embodiments of the present invention may contain the trisaccharide theanderose (G6-α-glucosyl sucrose), a substance found specifically in honey.

Non-limiting examples of other natural sugars that may be used in embodiments of the present invention include abequose, allose, allulose, altrose, apiose, arabinose, beet oligosaccharides, bifurcose, deoxyribose, dextrose(D-glucose), erlose, erythrose, erythrulose, fructose (levulose), fucose, fuculose, galactose, gentiobiose, gentiotriose, gentiotetraose, etc., gulose, hamamelose, inulobiose, inulotriose, inulotetraose, isomaltose, isomaltotriose, isomaltotetraose, isomaltopentaose, isomaltulose (palatinose), kestose, kojibiose, lactose, lactulose, laminaribiose, lyxose, mannose, maltose, maltotriose, maltotetraose, etc., maltulose, meletzitose, melibiose, methose, nigerose, nystose, panose, paratose, primeverose, psicose, raffinose, rhamnose, ribose, ribulose, rutinose, sorbinose, sorbose, soybean oligosaccharides, stachyose, sucrose, tagatose, talose, theanderose, threose, trehalose, turanose, xylobiose, xylotriose, etc., xylose, or xylulose, all of which may be used with acetylsalicylic acid in compositions according to embodiments of the present invention. The carbohydrates used in embodiments of the present invention may be of their respective D- or L-configurations.

In certain embodiments, non-limiting examples of sugar alcohols that may be used include allitol, arabitol, erythritol, galactitol, glycerol, glycol, iditol, inositol, isomalt, lactitol, maltotetraol, maltotriol, mannitol, ribitol, sorbitol, talitol, threitol, and xylitol. The sugar alcohols used in embodiments according to the present invention may be of their respective the D- or L-configurations. These sugar alcohols have the benefits of having low glycemic indices. Mannitol, for example, has been used to treat increased intracranial pressure. The following crystalloids may be used in formulations according to embodiments of the present invention: D5W, D10W, D50, D5 0.3% NS, D5 0.45% NS, 0.45% NS, D5 0.9% NS, 0.9% NS, 3% NaCl, D5RL, LR, NaHCO$_3$, and Xylitol solutions.

Formulations according to embodiments of the present invention may be fully dissolved in an aqueous solution and administered via the parenteral route. The following infusion fluids may be used in formulations according to embodiments of the present invention: D5W, D10W, D50, D5 0.3% NS, D5 0.45% NS, 0.45% NS, D5 0.9% NS, 0.9% NS, 3% NaCl, D5RL, LR, NaHCO3, and Xylitol solutions.

Next, the present invention will be described in further detail by means of examples, without intending to limit the scope of the present invention to these examples alone. The following are exemplary formulations of water-soluble acetylsalicylic acid compositions in accordance with the present invention.

Example 1

A cocrystal product of the present invention was prepared by weighing 352 mg of acetylsalicylic acid and 340 mg of L-theanine, and transferring the solids to an agate mortar. The solids were wetted with 500 µL of methanol, and hand-ground with a pestle until a dried crystalline mass was obtained. This product was characterized using differential scanning calorimetry ("DSC;" see FIG. 2), x-ray powder diffraction ("XRPD;" see FIG. 3), Fourier-transform infrared spectroscopy with attenuated total reflectance sampling ("FTIR-ATR;" see FIG. 4), and Raman spectroscopy with diffuse reflectance sampling ("RAM-DR;" see FIG. 5). In addition, 117 mg of the cocrystal product was found to dissolve in 13 mL of water, making the aqueous solubility approximately 9 mg/mL.

Example 2

The aqueous solution formed in Example 1 was poured in an evaporating dish, and allowed to dry completely. The DSC thermogram of the solid product is reflected in FIG. 2, the XRPD pattern is reflected in FIG. 3, the FTIR-ATR spectrum is reflected in FIG. 4, and the RAM-DR spectrum is reflected in FIG. 5.

Example 3

1.721 g of acetylsalicylic acid and 1.667 g of L-theanine were weighed and transferred into a large glass mortar. The solids were wetted with 20 mL of methanol, and hand-ground with a pestle until a dried crystalline mass was obtained. The DSC thermogram of the solid product is reflected in FIG. 2, the XRPD pattern is reflected in FIG. 3, the FTIR-ATR spectrum is reflected in FIG. 4, and the RAM-DR spectrum is reflected in FIG. 5. 752 mg of the cocrystal product was found to dissolve in 80 mL of water, making the aqueous solubility 9.4 mg/mL.

Aliquots of the aqueous solution were separately diluted in 1:1 v/v ratios with (a) pH 7.4 tromethamine buffer, (b) 0.9% saline solution, (c) 7.5% sodium bicarbonate solution, (d) 5% dextrose for injection, and (e) 50% dextrose for injection. The solutions were observed to remain physically unchanged over a six-day period, indicating compatibility of the cocrystal product with each of the infusion solutions.

Example 4

435 mg of acetylsalicylic acid and 424 mg of L-theanine were weighed into a 200 mL round-bottomed flask, and dissolved in 100 mL of water. The resulting clear solution was then dried using rotatory evaporation until a dried crystalline mass was obtained. The DSC thermogram of this solid product is reflected in FIG. 2, the XRPD pattern is reflected in FIG. 3, the FTIR-ATR spectrum is reflected in FIG. 4, and the RAM-DR spectrum is reflected in FIG. 5. 752 mg of the cocrystal product was found to dissolve in 80 mL of water, making the aqueous solubility 9.4 mg/mL.

Example 5

A cocrystal product of the present invention was prepared by weighing 353 mg of acetylsalicylic acid and 341 mg of D-theanine, and transferring the solids to an agate mortar. The solids were wetted with 500 µL of methanol, and hand ground with a pestle until a dried crystalline mass was obtained. Representative photomicrographs of the cocrystal product are shown in FIG. 6 This product was characterized using differential scanning calorimetry (DSC; see FIG. 7), x-ray powder diffraction (XRPD; see FIG. 8), Fourier-transform infrared spectroscopy with attenuated total reflectance sampling (FTIR-ATR; see FIG. 9), and Raman spectroscopy with diffuse reflectance sampling (RAM-DR; see FIG. 10). In addition, 68 mg of the cocrystal product was found to dissolve in 7.5 mL of water, making the aqueous solubility approximately 9 mg/mL.

Example 6

363 mg of acetylsalicylic acid and 354 mg of D-theanine were weighed into a 150 mL beaker, and dissolved in 100 mL of water. The resulting clear solution was then dried using rotatory evaporation until a dried crystalline mass was obtained. The DSC thermogram of this solid product is reflected in FIG. 7, the XRPD pattern is reflected in FIG. 8, the FTIR-ATR spectrum is reflected in FIG. 9, and the RAM-DR spectrum is reflected in FIG. 10.

Example 7

A cocrystal product of the present invention was prepared by weighing 368 mg of acetylsalicylic acid, 179 mg of L-theanine, and 178 mg of D-theanine, and transferring the solids to an agate mortar. The solids were wetted with 500 µL of methanol, and hand ground with a pestle until a dried crystalline mass was obtained. Representative photomicrographs of the cocrystal product are shown in FIG. 11. This product was characterized using differential scanning calorimetry (DSC; see FIG. 12), x-ray powder diffraction (XRPD; see FIG. 13), Fourier-transform infrared spectroscopy with attenuated total reflectance sampling (FTIR-ATR; see FIG. 14), and Raman spectroscopy with diffuse reflectance sampling (RAM-DR; see FIG. 15). In addition, 67 mg of the cocrystal product was found to dissolve in 9.5 mL of water, making the aqueous solubility approximately 7 mg/mL.

Example 8

358 mg of acetylsalicylic acid, 175 mg of L-theanine, and 174 mg of D-theanine were weighed into a 150-mL beaker, and dissolved in 100 mL of water. The resulting clear solution was then dried using rotatory evaporation until a dried crystalline mass was obtained. The DSC thermogram of this solid product is reflected in FIG. 12, the XRPD pattern is reflected in FIG. 13, the FTIR-ATR spectrum is reflected in FIG. 14, and the RAM-DR spectrum is reflected in FIG. 15.

The Tyndall effect is observed when particles of a solid are dispersed in water but not dissolved. Such an effect is strongly observed in dispersions of Bayer aspirin, Disprin, and Aspro Clear. No such strong effect is observed in water, or when cocrystal compositions according to embodiments of the present invention are dissolved in water. Colloids are particles which range in size from 1-1000 nm, and a Tyndall effect is created when a laser beam is scattered by its passage through a colloidal dispersion of non-dissolved particles. For such dispersions, the illumination of a visible path through the colloidal dispersion is observable. A true solution, such as water or a composition according to embodiments of the present invention dissolved in water, does not contain colloidal particles, and hence does not exhibit a strong Tyndall effect characteristic of colloidal dispersions. These findings, detailed below, as well as the preceding examples, demonstrate that compositions according to embodiments of the present invention dissolve to form true solutions in water, and do not merely disperse to form a colloidal dispersion.

Tyndall Experiment 1: Comparison of
Aspirin:(L)-Theanine Cocrystal Product with Disprin 300 mg of the aspirin:(L)-theanine cocrystal product was dissolved in 150 ml of water in one beaker and a 325 mg tablet of Disprin was dispersed in 150 ml of water in another beaker. A 514 nm laser beam was first passed through the aspirin:(L)-theanine cocrystal solution and then through the Disprin dispersion. A strong Tyndall effect was observed in the aqueous dispersion of Disprin, but was not observed with the composition according to the present invention dissolved in water.

An investigation regarding the degree of insoluble substance remaining after performance of the Tyndall effect experiment was carried out. The dispersions in the beakers were stirred to collect any undissolved solid in the center. An accumulation of undissolved solid formed at the bottom of the Disprin beaker, but not in the beaker containing aspirin (L)-theanine cocrystal product which displayed a crystal-clear solution.

Tyndall Experiment 2: Comparison of Aspirin:(L)-Theanine Cocrystal Product with Aspro Clear 300 mg of the aspirin:(L)-theanine cocrystal product was dissolved in 150 ml of water in one beaker and a 300 mg tablet of Aspro Clear was dispersed in 150 ml water in another beaker. A 514 nm laser beam was first passed through the aspirin:(L)-theanine cocrystal solution and then through the Aspro Clear dispersion. A strong Tyndall effect was observed in the aqueous dispersion of Aspro Clear, but was not observed with the composition according to the present invention dissolved in water.

An investigation regarding the degree of insoluble substance remaining after performance of the Tyndall effect experiment was carried out. The dispersions in the beakers were stirred to collect any undissolved solid in the center. An accumulation of undissolved solid formed at the bottom of the Aspro Clear beaker, but not in the beaker containing aspirin:(L)-theanine cocrystal product which exhibited a crystal-clear solution.

Tyndall Effect Experiment 3: Comparison of Aspirin:(L)-Theanine Cocrystal Product with Bayer Aspirin 300 mg of the aspirin:(L)-theanine cocrystal product was dissolved in 150 ml of water in one beaker and a 325 mg tablet of Bayer aspirin was dispersed in 150 ml of water in another beaker. A 514 nm laser beam was first passed through the aspirin:(L)-theanine cocrystal solution and then through the Bayer aspirin dispersion. A strong Tyndall effect was observed in the aqueous dispersion of Bayer aspirin, but was not observed with the composition according to the present invention dissolved in water.

An investigation regarding the degree of insoluble substance remaining after performance of the Tyndall effect experiment was carried out. The dispersions in the beakers were stirred to collect any undissolved solid in the center. An accumulation of undissolved solid formed at the bottom of the Bayer aspirin beaker, but not in the beaker containing aspirin:(L)-theanine cocrystal product which displayed a crystal-clear solution.

Tyndall Effect Experiment 4: Comparison of Aspirin:(L)-Theanine Cocrystal Product with Water 300 mg of the aspirin:(L)-theanine cocrystal product was dissolved in 150 ml of water in one beaker and 150 ml of water alone was place in another beaker. A 514 nm laser beam was first passed through the aspirin: (L)-theanine cocrystal solution and then through the water. A strong Tyndall effect was not observed with water, nor was it observed with the composition according to the present invention dissolved in water. Both water and the aspirin:(L)-theanine cocrystal product exhibited crystal-clear solutions and were indistinguishable from one other.

An investigation regarding the degree of insoluble substance remaining after performance of the Tyndall effect experiment was carried out. The dispersion in the beaker containing the dissolved aspirin:(L)-theanine cocrystal product was stirred to collect any undissolved solid in the center. No undissolved solids were observed at the bottom of the beaker with the aspirin:(L)-theanine cocrystal product. Both water and the aspirin:(L)-theanine cocrystal product produced crystal-clear solutions and were indistinguishable from one other.

Tyndall Effect Experiment 5: Comparison of Aspirin:(D)-Theanine Cocrystal Product with Dispirin 300 mg of the aspirin:(D)-theanine cocrystal product was dissolved in 150 ml of water in one beaker and a 325 mg tablet of Disprin was dispersed in 150 ml of water in another beaker. A 514 nm laser beam was first passed through the aspirin:(D)-theanine cocrystal solution and then through the Disprin dispersion. A strong Tyndall effect was observed in the aqueous dispersion of Disprin, but was not observed with the composition according to the present invention dissolved in water.

An investigation regarding the degree of insoluble substance remaining after performance of the Tyndall effect experiment was carried out. The dispersions in the beakers were stirred to collect any undissolved solid in the center. An accumulation of undissolved solid formed at the bottom of the Disprin beaker, but not in the beaker containing aspirin (D)-theanine cocrystal product which displayed a crystal-clear solution.

Tyndall Effect Experiment 6: Comparison of Aspirin:(D)-Theanine Cocrystal Product with Aspro Clear 300 mg of the aspirin:(D)-theanine cocrystal product was dissolved in 150 ml of water in one beaker and a 300 mg tablet of Aspro Clear was dispersed in 150 ml water in another beaker. A 514 nm laser beam was first passed through the aspirin:(D)-theanine cocrystal solution and then through the Aspro Clear dispersion. A strong Tyndall effect was observed in the aqueous dispersion of Aspro Clear, but was not observed with the composition according to the present invention dissolved in water.

An investigation regarding the degree of insoluble substance remaining after performance of the Tyndall effect experiment was carried out. The dispersions in the beakers were stirred to collect any undissolved solid in the center. An accumulation of undissolved solid formed at the bottom of the Aspro Clear beaker, but not in the beaker containing aspirin:(D)-theanine cocrystal product which displayed a crystal-clear solution.

Tyndall Effect Experiment 7: Comparison of Aspirin:(D)-Theanine Cocrystal Product with Bayer Aspirin 300 mg of the aspirin:(D)-theanine cocrystal product was dissolved in 150 ml of water in one beaker and a 325 mg tablet of Bayer aspirin was dispersed in 150 ml of water in another beaker. A 514 nm laser beam was first passed through the aspirin:(D)-theanine cocrystal solution and then through the Bayer aspirin dispersion. A strong Tyndall effect was observed in the aqueous dispersion of Bayer aspirin, but was not observed with the composition according to the present invention dissolved in water.

An investigation regarding the degree of insoluble substance remaining after performance of the Tyndall effect experiment was carried out. The dispersions in the beakers were stirred to collect any undissolved solid in the center. An accumulation of undissolved solid formed at the bottom of the Bayer aspirin beaker, but not in the beaker containing aspirin (D)-theanine cocrystal product which displayed a crystal-clear solution.

Tyndall Effect Experiment 8: Comparison of Aspirin:(D)-Theanine Cocrystal Product with Water 300 mg of the aspirin:(D)-theanine cocrystal product was dissolved in 150 ml of water in one beaker and 150 ml of water alone was placed in another beaker. A 514 nm laser beam was first passed through the aspirin:(D)-theanine cocrystal solution and then through the water. A strong Tyndall effect was not observed with water, nor was it observed with the composition according to the present invention dissolved in water. Both water and the aspirin:(D)-theanine cocrystal product produced crystal-clear solutions and were indistinguishable from one other.

An investigation regarding the degree of insoluble substance remaining after performance of the Tyndall effect experiment was carried out. The dispersion in the beaker containing the dissolved aspirin: (D)-theanine cocrystal product was stirred to collect any undissolved solid in the center. No undissolved solids were observed at the bottom of the beaker with the aspirin:(D)-theanine cocrystal product. Both water and the aspirin:(D)theanine cocrystal product produced crystal-clear solutions and were indistinguishable from one other.

Tyndall Effect Experiment 9: Comparison of Aspirin:(DL)-Theanine Cocrystal Product with Disprin 300 mg of the aspirin:(DL)-theanine cocrystal product was dissolved in 150 ml of water in one beaker and a 325 mg tablet of Disprin was dispersed in 150 ml of water in another beaker. A 514 nm laser beam was first passed through the aspirin:(DL)-theanine cocrystal solution and then through the Disprin dispersion. A strong Tyndall effect was observed in the aqueous dispersion of Disprin, but was not observed with the composition according to the present invention dissolved in water.

An investigation regarding the degree of insoluble substance remaining after performance of the Tyndall effect experiment was carried out. The dispersions in the beakers were stirred to collect any undissolved solid in the center. An accumulation of undissolved solid formed at the bottom of the Disprin beaker, but not in the beaker containing aspirin:(DL)-theanine cocrystal product which displayed a crystal-clear solution.

Tyndall Effect Experiment 10: Comparison of Aspirin:(DL)-Theanine Cocrystal Product with Aspro Clear 300 mg of the aspirin:(DL)-theanine cocrystal product was dissolved in 150 ml of water in one beaker and a 300 mg tablet of Aspro Clear was dispersed in 150 ml water in another beaker. A 514 nm laser beam was first passed through the aspirin:(DL)-theanine cocrystal solution and then through the Aspro Clear dispersion. A strong Tyndall effect was observed in the aqueous dispersion of Aspro Clear, but was not observed with the composition according to the present invention dissolved in water.

An investigation regarding the degree of insoluble substance remaining after performance of the Tyndall effect experiment was carried out. The dispersions in the beakers were stirred to collect any undissolved solid in the center. An accumulation of undissolved solid formed at the bottom of the Aspro Clear beaker, but not in the beaker containing aspirin (DL)-theanine cocrystal product which displayed a crystal-clear solution.

Tyndall Effect Experiment 11: Comparison of Aspirin:(DL)-Theanine Cocrystal Product with Bayer Aspirin 300 mg of the aspirin:(DL)-theanine cocrystal product was dissolved in 150 ml of water in one beaker and a 325 mg tablet of Bayer aspirin was dispersed in 150 ml of water in another beaker. A 514 nm laser beam was first passed through the aspirin:(DL)-theanine cocrystal solution and then through the Bayer aspirin dispersion. A strong Tyndall effect was observed in the aqueous dispersion of Bayer aspirin, but was not observed with the composition according to the present invention dissolved in water.

An investigation regarding the degree of insoluble substance remaining after performance of the Tyndall effect experiment was carried out. The dispersions in the beakers were stirred to collect any undissolved solid in the center. An accumulation of undissolved solid formed at the bottom of the Bayer aspirin beaker, but not in the beaker containing aspirin (DL)-theanine cocrystal product which displayed a crystal-clear solution.

Tyndall Effect Experiment 12: Comparison of Aspirin:(DL)-Theanine Cocrystal Product with Water 300 mg of the aspirin:(DL)-theanine cocrystal product was dissolved in 150 ml of water in one beaker and 150 ml of water alone was placed in another beaker. A 514 nm laser beam was first passed through the aspirin:(DL)-theanine cocrystal solution and then through the water. A strong Tyndall effect was not observed with water, nor was it observed with the composition according to the present invention dissolved in water. Both water and the aspirin:(DL)-theanine cocrystal product produced crystal-clear solutions and were indistinguishable from one other.

An investigation regarding the degree of insoluble substance remaining after performance of the Tyndall effect experiment was carried out. The dispersion in the beaker containing the dissolved aspirin:(DL)-theanine cocrystal product was stirred to collect any undissolved solid in the center. No undissolved solids were observed at the bottom of the beaker with the aspirin:(DL)-theanine cocrystal product. Both water and the aspirin:(DL)-theanine cocrystal product produced crystal-clear solutions and were indistinguishable from one other.

Derivatives prepared using compositions according to embodiments of the present invention can be administered via intravenous, intramuscular, intradermal, subcutaneous, intraperitoneal, intraarticular, sublingual, subconjunctival, and intravitreal routes, or in the form of eye drops, orally, topically, rectally, via nasal spray, inhalation, and nanoparticle delivery systems.

The pharmaceutical compositions according to embodiments of the present invention may be prepared as oral solids (tablets, oral disintegrating tablets, effervescent tablets, capsules), oral liquids, hard or soft gelatin capsules, quick dissolve, controlled released, modified released, syrups, suspensions, granules, wafers (films), pellets, lozenges, powders, chewables, suppositories, ointments, solutions, parenteral/injectable powders or granules that are pre-mixed or reconstituted, lotions, gels, creams, foams, and nanoemulsions.

The pharmaceutical compositions according to embodiments of the present invention may be combined with lipooxygenase inhibitor agents, natural lipooxygenase inhibitors, anti-hypertensive agents, anti-hyperlipidemic agents, anti-hypertensive/anti-hyperlipidemic agents, anti-triglyceride agents, anti-migraine agents, blood modifier agents, especially thrombolytic agents and platelet aggregation inhibitor agents, anti-neoplastic agents, anti-psychotic agents, anti-anxiety agents, anti-convulsant agents, anti-Parkinsonian agents, anti-diabetic agents, anti-inflammatory agents such as corticosteroids, anti-pyretic agents excluding NSAIDS (NSAIDS when combined with aspirin, negate the effects of aspirin), anti-rheumatic agents excluding NSAIDS, agents for treatment of symptoms associated with premenstrual syndrome excluding NSAIDS, anti-arrhythmic agents, digitalis glycosides, anti-anginal agents (nitrates, anti-platelet agents, beta blockers, calcium channel blockers and ranolazine), analgesic agents, musculoskeletal relaxants, anti-infective agents especially antibiotics, parenteral nutritional agents, magnesium, Co-enzyme $Q_{10}$, sarcosine, amino acids, vitamins (except vitamin K), and agents used to treat diseases associated with excess amounts of glutamate such as, but not limited to amyotrophic lateral sclerosis, cerebrovascular dementia, and with brain injuries, as occurs with non-hemorrhagic strokes or physical injuries. The pharmaceutical compositions of the invention with theanine are not limited to these agents.

Intravenous formulations according to embodiments of the present invention include new compounds that are combined lipooxygenase/cyclooxygenase inhibitors for treatment of, among other things, myocardial ischemia, myocardial infarction, cerebral ischemia, stroke, atherosclerosis, retinal ischemia, rheumatoid arthritis, osteoarthritis, inflammatory bowel disease, and certain types of cancers.

Embodiments of the present invention have other potential clinical applications including, but not limited to the following: cardiovascular (treatment of acute coronary syndrome, treatment of acute myocardial infarction, adjunctive therapy in revascularization procedures: percutaneous transluminal coronary angioplasty, coronary artery bypass grafts, carotid enarterectomy, and stent implantation); neurologic (treatment of acute ischemic stroke); dysphagia (from any etiology); rheumatologic (rheumatoid arthritis, ankylosing spondylitis, spondyloarthropathies, pleurisy and arthritis of systemic lupus erythematous, psoriatic arthritis, fibromyalgia, Reiter's syndrome, osteoarthritis, Lyme arthritis and gonorrhea arthritis); anti-inflammatory (epididymitis, Bornholm's disease (coxsackie myocarditis), acute pericarditis, Dressler's syndrome, acute rheumatic fever, Ross River fever); pain management (marine envenomations such as from jellyfish, sea urchins, star fish, Portuguese man-of-wars, fire corals, sea anemones, lionfish, stonefish, and stingrays; Osgood-Schlatter disease, idiopathic (primary) erythromelalgia, burns, acute renal colic, trigeminal neuralgia, bone pain (osteoid osteomas, Pagets disease, sickle cell anemia), spinal stenosis, metastatic disease, intractable headaches, radiculopathies, and other chronic pain syndromes; as an adjuvant to morphine for patient-controlled analgesia (PCA); ophthalmologic (retinal ischemia and retinal occlusion); emergent use (in ambulances, hospital emergency rooms and critical care units, doctors' offices, air travel, in the wilderness, etc.); with intubated patients and patients with severely compromised bowel function, excluding Crohn's disease and ulcerative colitis; as an anti-pyretic for high grade temperatures, excluding malignant hyperthermia; for prevention of post-anesthetic shivering; for closure of patent ductus arteriosus; for familial cylindromatosis; for inhibition of angiogenesis; for inhibition of niacin flushing; as an adjuvant to thrombolytic therapy for the treatment of frostbite; the treatment of rare diseases (including Kawasaki disease, Riedel thyroiditis, adult-onset Still's disease, Kikuchi-Fujimoto disease, focal myositis, Weber-Christian disease, and adhesive arachnoiditis); substantial protection against hepatotoxic effects from drugs, alcohol, herbs, toxins, chemicals, obesity-related liver disease and radiation-induced liver disease; and for providing anti-HIV effects.

Embodiments of the present invention may be employed to provide substantial protection against a wide variety of medical conditions, including but not limited to, the hepatotoxic effects from Tylenol, statins, antiretrovirals, alcohol, and other drugs, toxins, herbs, and chemicals that are capable of inducing hepatoxicity; obesity-related liver disease; and radiation-induced liver disease.

Cocrystals according to embodiments of the present invention may be used to improve one or more physical properties, such as solubility, stability, and dissolution rate, of the active pharmaceutical ingredient of a selected treatment or prevention.

While specific embodiments of the invention have been shown and described in detail to illustrate the application of the principles of the invention, it will be understood that the invention may be embodied otherwise without departing from such principles.

What is claimed is:

1. A method of treating rheumatoid arthritis by administering an effective amount of a water-soluble composition comprising: a cocrystal composition containing a quantity of acetylsalicylic acid and a quantity of a theanine enantiomer selected from the group consisting of L-theanine, D-theanine, and DL-theanine.

2. The method of claim 1, wherein said quantity of acetylsalicylic acid comprises about 50% by weight of said mixture.

3. The method of claim 1, wherein said mixture has an aqueous solubility of at least about 9.0 mg/mL.

4. The method of claim 1, wherein said mixture has an aqueous solubility of at least about 9.4 mg/mL.

5. The method of claim 1, wherein said mixture further comprises a sugar alcohol.

6. The method of claim 5, wherein said sugar alcohol has an L-configuration.

7. The method of claim 1, wherein said water soluble composition is combined with an agent for treatment of arthritis prior to administration.

8. The method of claim 1, wherein said treatment is achieved by an administration means selected from the group consisting of intravenous route, intramuscular route, intradermal route, subcutaneous route, intraperitoneal route, intraarticular route, sublingual route, subconjunctival route, and intravitreal route.

9. A method of treating rheumatoid arthritis by administering an effective amount of a water-soluble composition comprising a cocrystal composition containing a quantity of acetylsalicylic acid and a quantity of L-Theanine, the composition made by a process comprising the steps of:
- providing a quantity of acetylsalicylic acid;
- adding a quantity of L-Theanine to said quantity of acetylsalicylic acid to form a mixture comprising said quantity of acetylsalicylic acid and said L-Theanine;
- wetting said mixture; and grinding said mixture for a length of time sufficient to produce a dried crystalline mass.

10. The method of claim 9, wherein said treatment is achieved by an administration means selected from the group consisting of intravenous route, intramuscular route, intradermal route, subcutaneous route, intraperitoneal route, intraarticular route, sublingual route, subconjunctival route, and intravitreal route.

11. A method of treating rheumatoid arthritis by administering an effective amount of a water-soluble composition comprising a cocrystal composition containing a quantity of acetylsalicylic acid and a quantity of L-Theanine, the composition made by a process comprising the steps of:
- providing a quantity of acetylsalicylic acid;
- adding a quantity of L-Theanine to said quantity of acetylsalicylic acid to form a mixture comprising said quantity of acetylsalicylic acid and said quantity of L-Theanine;
- dissolving said mixture in a quantity of a first solvent to form a solution; and
- drying said solution for a length of time sufficient to produce a dried crystalline mass of an aspirin-theanine cocrystal composition.

12. The method of claim 11, wherein said treatment is achieved by an administration means selected from the group consisting of intravenous route, intramuscular route, intradermal route, subcutaneous route, intraperitoneal route, intraarticular route, sublingual route, subconjunctival route, and intravitreal route.

13. A method of treating rheumatoid arthritis by administering an effective amount of a water-soluble aspirin-theanine cocrystal composition, the composition made by a method comprising the steps of:
- providing a quantity of acetylsalicylic acid;
- adding a quantity of a theanine enantiomer selected from the group consisting of L-theanine, D-theanine, and DL-theanine to said quantity of acetylsalicylic acid to form a mixture comprising said quantity of acetylsalicylic acid and said enantiomer of theanine;
- wetting said mixture; and
- grinding said mixture for a length of time sufficient to produce a dried crystalline mass.

14. The method of claim 13, wherein said treatment is achieved by an administration means selected from the group consisting of intravenous route, intramuscular route, intradermal route, subcutaneous route, intraperitoneal route, intraarticular route, sublingual route, subconjunctival route, and intravitreal route.

15. A method of treating rheumatoid arthritis by administering an effective amount of a water-soluble aspirin-theanine cocrystal composition, the composition made by a method comprising the steps of:
- providing a quantity of acetylsalicylic acid;
- adding a quantity of a theanine enantiomer selected from the group consisting of L-theanine, D-theanine, and DL-theanine to said quantity of acetylsalicylic acid to form a mixture comprising said quantity of acetylsalicylic acid and said quantity of a theanine enantiomer;
- dissolving said mixture in a quantity of a first solvent to form a solution; and
- drying said solution for a length of time sufficient to produce a dried crystalline mass of an aspirin-theanine cocrystal composition.

16. The method of claim 15, wherein said treatment is achieved by an administration means selected from the group consisting of intravenous route, intramuscular route, intradermal route, subcutaneous route, intraperitoneal route, intraarticular route, sublingual route, subconjunctival route, and intravitreal route.

* * * * *